United States Patent
Pai et al.

(10) Patent No.: US 7,435,391 B2
(45) Date of Patent: Oct. 14, 2008

(54) LIGHT-MEDIATED MICRO-CHEMICAL REACTORS

(75) Inventors: Chien-Shing Pai, Bridgewater, NJ (US); Stanley Pau, Hoboken, NJ (US)

(73) Assignee: Lucent Technologies Inc., Murray Hill, NJ (US)

( * ) Notice: Subject to any disclaimer, the term of this patent is extended or adjusted under 35 U.S.C. 154(b) by 773 days.

(21) Appl. No.: 10/444,578

(22) Filed: May 23, 2003

(65) Prior Publication Data

US 2004/0234424 A1    Nov. 25, 2004

(51) Int. Cl.
*B01J 19/00* (2006.01)
*G01N 1/10* (2006.01)
*G01J 5/02* (2006.01)
*G01N 21/00* (2006.01)
*G01J 3/00* (2006.01)

(52) U.S. Cl. .......... 422/130; 422/55; 422/68.1; 422/129; 422/131; 356/51; 356/244; 356/246; 356/436; 356/437; 356/439; 356/440; 250/343; 250/373

(58) Field of Classification Search ............ 422/131; 204/192.27; 356/246, 239.6; 250/339.11, 250/356.1
See application file for complete search history.

(56) References Cited

U.S. PATENT DOCUMENTS

| | | | |
|---|---|---|---|
| 4,553,243 A | 11/1985 | Rosenwaks et al. | 372/89 |
| 4,653,062 A | 3/1987 | Davis et al. | 372/89 |
| 4,688,893 A * | 8/1987 | Laakmann | 385/125 |
| 5,165,005 A * | 11/1992 | Klainer et al. | 385/129 |
| 5,378,449 A | 1/1995 | Dinges | 423/579 |
| 5,589,136 A | 12/1996 | Northrup et al. | 422/102 |
| 5,595,712 A * | 1/1997 | Harbster et al. | 422/129 |
| 5,726,752 A * | 3/1998 | Uno et al. | 356/246 |
| 5,846,842 A * | 12/1998 | Herron et al. | 436/518 |
| 5,870,422 A | 2/1999 | Florentino et al. | 372/89 |
| 5,876,675 A * | 3/1999 | Kennedy | 422/99 |
| 5,922,591 A * | 7/1999 | Anderson et al. | 435/287.2 |
| 5,974,072 A | 10/1999 | Hartlove et al. | 372/89 |
| 6,099,805 A | 8/2000 | Hartlove | 422/122 |
| 6,154,478 A | 11/2000 | Vetrovec | 372/89 |

(Continued)

FOREIGN PATENT DOCUMENTS

EP    0 599 248 A1    6/1994

(Continued)

OTHER PUBLICATIONS

U.S. Appl. No. 11/148,549, Pau et al., filed Jun. 9, 2005.

(Continued)

*Primary Examiner*—Jill Warden
*Assistant Examiner*—Neil Turk
(74) *Attorney, Agent, or Firm*—John F. McCabe (57) ABSTRACT

A chemical reactor includes two substrates that are joined along a surface and a chemical reaction chamber formed between the substrates. The chemical reaction chamber has a hollow interior and one or more light reflectors located along walls of the hollow interior. The chemical reaction chamber has one or more inputs to transport fluid into the hollow interior and an output to transport fluid out of the hollow interior. The one or more light reflectors cause light rays to make multiple crossings of the hollow interior as a result of reflections off the one or more reflectors.

18 Claims, 7 Drawing Sheets

U.S. PATENT DOCUMENTS

| | | | |
|---|---|---|---|
| 6,221,226 B1* | 4/2001 | Kopf-Sill | 204/602 |
| 6,224,786 B1 | 5/2001 | Stelman | 252/183.14 |
| 6,248,539 B1* | 6/2001 | Ghadiri et al. | 435/7.1 |
| 6,352,838 B1 | 3/2002 | Krulevitch et al. | 435/34 |
| 6,377,600 B1 | 4/2002 | Flegal | 372/89 |
| 6,438,279 B1* | 8/2002 | Craighead et al. | 385/12 |
| 6,490,034 B1* | 12/2002 | Woias et al. | 356/246 |
| 6,974,673 B2* | 12/2005 | Lockhart | 435/7.1 |
| 2002/0181837 A1* | 12/2002 | Wang et al. | 385/16 |
| 2003/0020915 A1* | 1/2003 | Schueller et al. | 356/436 |

FOREIGN PATENT DOCUMENTS

| | | |
|---|---|---|
| EP | 0 891 022 A1 | 1/1999 |
| EP | 0 891 025 A2 | 1/1999 |
| EP | 0 893 704 A2 | 1/1999 |
| EP | 1 059 709 A2 | 12/2000 |
| WO | WO 80/00922 | 5/1980 |
| WO | WO 90/07810 | 7/1990 |
| WO | WO 90/08414 | 7/1990 |
| WO | WO 97/00726 | 1/1997 |

OTHER PUBLICATIONS

Harendt, C., et al., "Silicon fusion bonding and its characterization," J. Micromech. Microeng., vol. 2, pp. 113-116, 1992.

Low temperature wafer anodic bonding, by J. Wei et al., J. Micromech. Microeng., Vo. 13 (2003) pp. 217-222.

Online publication entitled: "*Luminescence Analysis*," published by Biothema in Sep. 2002 at : www.biothema.com/luminescence analysis, 1 page.

Online publication titled: "*An Introduction to Chemiluminescence and Bioluminescence Measurements*," published by "Communication Technology" prior to Apr. 8, 2003 at: www.comm-tec.com/library/ App Notes/ctd/Chemiluminescence and Bioluminesance Measurements, pp. 1-11.

Application Note of Waco Pure Chemical Industries Ltd. entitled : "*Performance of a typical luminescence application demonstrated on two examples of Firefly Luciferase Assays*," (Firefly Luciferase Assay, Doc. 391 551), Nov. 2000, pp. 1-4.

Wood, K.V., Lam, Y.A., Seliger, H.H., McElroy, W.D., "*Complementary DNA Coding Click Beetle Luciferases Can Elicit Bioluminescence of Difference Colors*," Science, vol. 244, May 1989, pp. 700-702.

Cool, T.A., Falk, T.J., Stephens, R.R., "*DF-$CO_2$ and HF-$CO_2$ Continuous-Wave Chemical Lasers*," Applied Physics Letters, vol. 15, No. 10, Nov. 15, 1969, pp. 318-320.

White, E.H., Steinmetz, M.G., Miano, J.D., Wildes, P.D. and Morland, R., "*Chemi-and Bioluminescence of Firefly Luciferin*," Journal of the American Chemical Society, Apr. 23, 1980, pp. 3199-3208.

Online Publication by Michigan State University entitled: "*Reactions of Alkanes*," Chemical Reactivity, http://cem.msu.edu/-reusch/VirtualText/funerx1.htm, (Apr. 23, 2003), p. 1-4.

Gomi, K. and Kajiyama, N., "*Oxyluciferin, a Luminescense Product of Firefly Luciferase, Is Enzymatically Regenerated into Luciferin*," The Journal of Biological Chemistry, vol. 276, No. 39, Issue of Sep. 28, 2001, pp. 36508-36513.

* cited by examiner

LIGHT-MEDIATED MICRO-CHEMICAL REACTORS

BACKGROUND

1. Field of the Invention

The invention relates to chemical reactors.

2. Discussion of the Related Art

Chemical reactors are structures for carrying out chemical reactions under controlled conditions. A chemical reactor includes a substantially closed chemical reaction chamber (CRC) where the chemical reaction occurs. A chemical reactor may also include a device for mixing different types of reactant molecules prior to injection of the reactant molecules into the CRC.

The CRC regulates reaction conditions so that the production of byproducts during the chemical reaction is controlled. By regulating the reaction conditions, a CRC often is able to control the rate of the production of particular byproducts. By regulating reaction conditions, a CRC may selectively produce a particular byproduct when several competing reaction pathways exist for different byproducts.

In many CRCs, either a heater or a spark generator initiates the chemical reaction. Heaters and spark generators provide some control over chemical reaction rates, but typically provide less control over selection of reaction pathway when several pathways compete for the available reactant molecules.

BRIEF SUMMARY

Various embodiments provide micro-chemical reactors where optically stimulated reactions proceed. The micro-chemical reactors include structures for increasing the optical path of light therein so that the light is more efficient at stimulating chemical reactions. Since light initiates the chemical reaction, some micro-chemical reactors are very selective at initiating specific chemical reaction pathways in the presence of competing pathways.

One embodiment features a chemical reactor including two substrates that are joined along a surface and a chemical reaction chamber formed between the substrates. The chemical reaction chamber has a hollow interior and one or more light reflectors located along walls of the hollow interior. The chemical reaction chamber has one or more inputs to transport fluid into the hollow interior and an output to transport fluid out of the hollow interior. The one or more light reflectors cause light rays to make multiple crossings of the hollow interior as a result of reflections off the one or more reflectors.

Another embodiment features a process for operating a chemical reactor. The process includes pumping a liquid having dissolved reactant molecules into a chemical reaction chamber formed between two joined substrates. Each substrate includes dielectric and/or semiconductor. The process also includes providing conditions in the chemical reaction chamber that produce a wavelength of light that stimulates a chemical reaction of the reactant molecules. A portion of the light undergoes multiple reflections off optical reflectors located along walls of the chemical reaction chamber.

BRIEF DESCRIPTION OF THE DRAWINGS

In the Figures and text, same reference numerals refer to elements having similar functions.

DETAILED DESCRIPTION OF ILLUSTRATIVE EMBODIMENTS

Various embodiments provide micro-chemical reactors (MCRs) in which light controls a chemical reaction's rate. The MCRs include small chemical reaction chambers adapted for carrying out reactions with small quantities of reactant molecules. For that reason, the light that controls the chemical reaction must propagate along short straight-line paths. Such short paths provide low probabilities for interactions between the light and the reactant molecules. To compensate for the short paths, the MCRs include optical reflectors. The reflectors increase the effective lengths of light paths in the MCRs and thus, increase the rates for interactions between light and reactant molecules. Various MCRs provide devices for carrying out light-controlled chemical reactions or for chemical-stimulated emission light sources.

Figure 1:
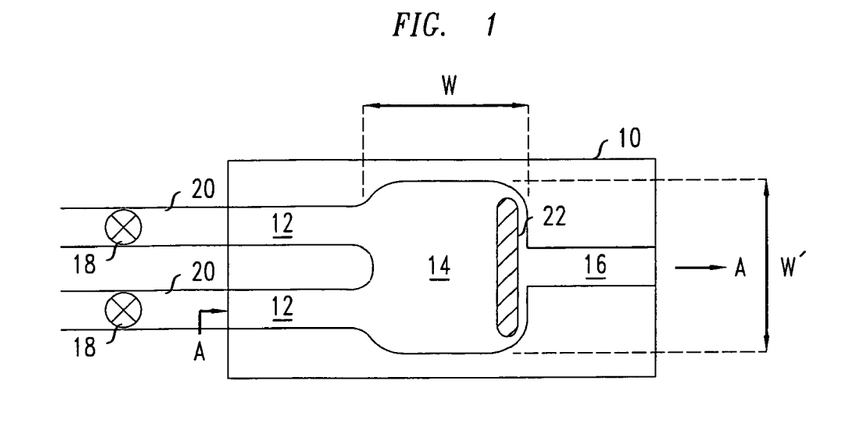
FIG. 1 is a top view of a light-controlled micro-chemical reactor (MCR)

FIG. 1 shows a light-controlled MCR 10. The MCR 10 includes one or more inputs 12 for fluids that carry chemical reactant molecules, e.g., as dissolved molecules. The fluids may be either gases or liquids and are pumped into the inputs 12 by external pumping devices 18 and external channels 20. The MCR also includes a hollow chemical reaction microchamber (CRC) 14, and one or more outputs 16 for removing fluid byproducts produced by a chemical reaction in the CRC 14. Exemplary CRCs 14 are hollow planar structures having lateral widths, W and W', in the range of 10 microns to 500 microns or less and heights, H, in the range of 20 microns to 300 microns. The small volumes of such CRCs 14 are advantageous for carrying out chemical reactions with small quantities of reactant molecules, e.g., small quantities of rare or costly biological molecules.

Some embodiments of MCR 10 include an optically transparent window 22 that enables the external introduction of control light into CRC 14. The control light often has a wavelength that is resonantly absorbed by reactant molecules, and thus, that is selective in stimulating a desired chemical reaction. Thus, the window 22 potentially enables selectively stimulating a desired reaction in the presence of competing reactions. For that reason, the window 22 may enable selection of reactions that would not otherwise, produce acceptable quantities of desired byproducts due to competition. The window 22 also enables spectral monitoring of the chemical reaction proceeding in the CRC 14.

Unfortunately, the CRC 14 has linear dimensions that are often too small for adequate interaction times between light and reactants located in the CRC 14. In the absence of other structures much control/stimulating light would be wasted rather than used in stimulating chemical reactions. The CRC 14 includes optical structures to reduce such waste, i.e., structures that lengthen effective optical paths inside the CRC 14.

FIGS. 2-5 provide cross-sectional views of various embodiments of CRC 14 of FIG. 1 along line AA.

Referring to FIGS. 2-5, optical reflectors 24, 26 are located along facing walls of CRC 14. The optical reflectors 24, 26 increase the effective optical path length for light rays in CRC 14, because reflections off the reflectors 24, 26 enable light rays to make multiple crossings of the hollow interior of the CRC 14 before being absorbed. In particular, the reflectors 24, 26 are located to cause a light ray 28 introduced via window 22 to have near normal incidence on the reflector 26. The near normal incidence causes the light ray 28 to undergo many reflections off the reflectors 24, 26. In various embodiments, the reflectors 24, 26 are either located inside the chemical reaction micro-chamber 14, or protected from the CRC 14 by a transparent protective layer, e.g., a dielectric layer. In both cases, the reflectors 24, 26 are located along the inside walls of the CRC 14.

Exemplary reflectors 24, 26 include thin films of metals such as gold, silver, aluminum, or copper and multi-layer dielectric structures with wavelength selective reflectivities. Herein, a reflector reflects, at least, 60% of normally incident light in a selected visible or near IR wavelength range. The reflectors 24, 26 reflect 75%, 80%, 90% or more of such normally incident light. The reflectors may include a transparent dielectric coating, e.g., of silicon nitride, to protect their surfaces from the reactant molecules found in the CRC 14.

Figure 2:
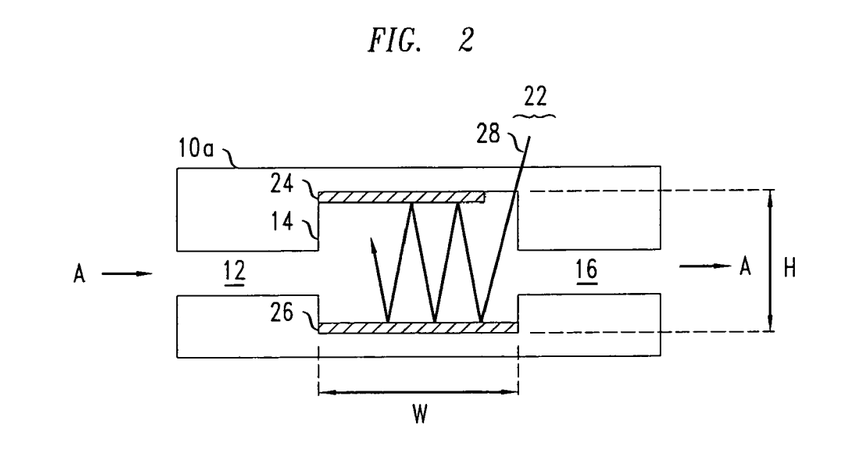
FIG. 2 is a cross-sectional view of one embodiment of the light-controlled MCR of FIG. 1.

Referring to FIG. 2, the MCR 10a has a single fluid input 12A and thus, requires either a fluid with a single reactant or a fluid with several premixed reactants.

Figure 3:
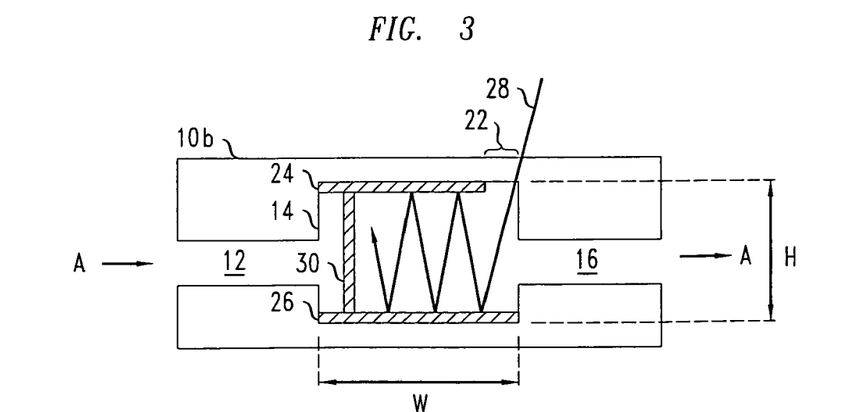
FIG. 3 is a cross-sectional view of another embodiment of the light-controlled MCR of FIG. 1.
Figure 4:
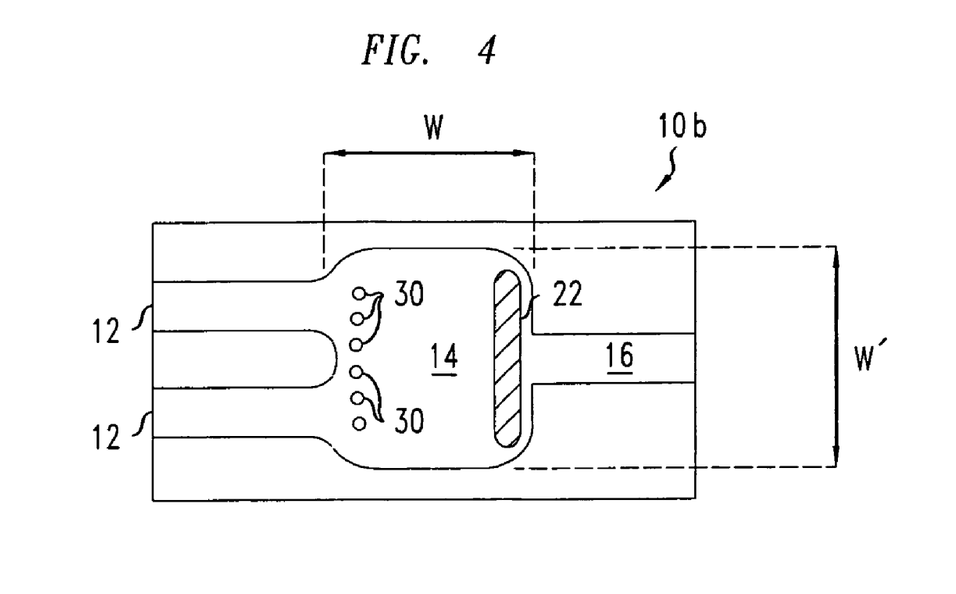
FIG. 4 is a top view of a section through the light-controlled MCR of FIG. 3.

Referring to FIGS. 3 and 4, MCRs 10b, 10c have multiple inputs 12 for introducing two or more fluids. The fluids may transport different types of reactant molecules that are subsequently mixed due to physical structures in the MCRs 10b, 10c. In particular, the MCRs 10b, 10c include arrays of flow obstructions 30, e.g., posts, which interrupt smooth lamellar fluid flows and cause fluid mixing. The flow obstructions 30, e.g., may cause mixing of the species of reactant molecules that chemically react. The widths and spacings of the flow obstructions 30 are determined by the desired mixing and depend upon the fluid viscosities and flow rates.

MCR 10b of FIG. 3 has flow obstructions 30 located in the hollow interior of CRC 14. The flow obstructions 30 are located near inputs 12 where they interfere with fluid flow and causing mixing of fluids delivered from different ones of the inputs 12. The flow obstructions are also located near an edge of the CRC 14 where they will interfere less with light rays 28 reflecting across the CRC 14. The flow obstructions 30 may be near an edge of the CRC 14 opposite to the edge where window 22 introduces light therein.

Figure 5:
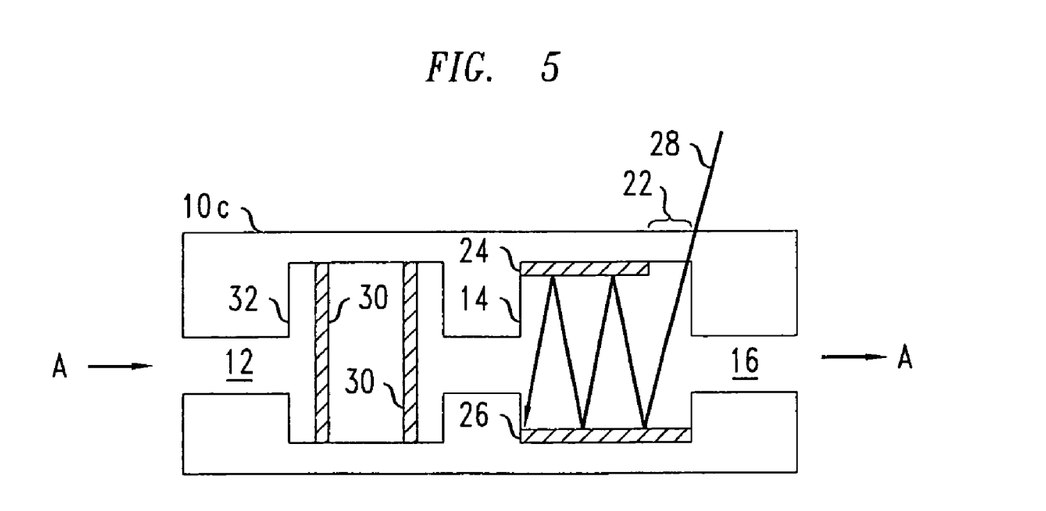
FIG. 5 is a cross-sectional view of yet another embodiment of the light-controlled MCR of FIG. 1.

MCR 10c of FIG. 5 has flow obstructions 30 located in a mixing chamber 32 that is separate from CRC 14. The fluids from the different inputs 12 are premixed in the mixing chamber 32 prior to being delivered to the CRC 14.

Referring to FIGS. 2-5, some embodiments of MCRs 10a-10c are configured for catalyzed reactions. The chemical catalysts are either transported in the same fluids that carry reactant molecules or are chemically bound to surfaces of the hollow CRC 14. The chemical catalysts may also be chemically bound to the surfaces of the flow obstructions 30 located in the CRC 14 of MCR 10b.

Figure 6:
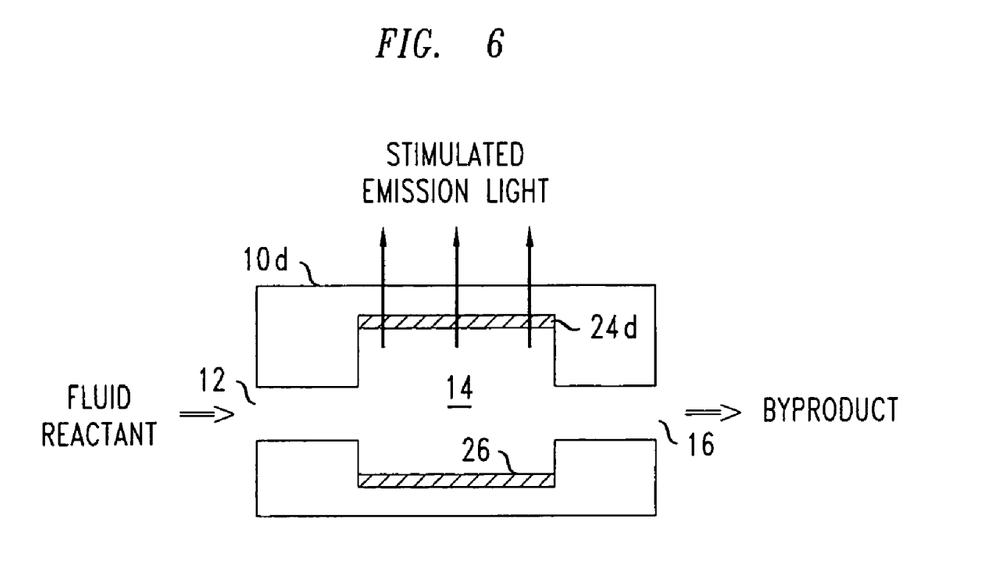
FIG. 6 is a cross-sectional view of a stimulated emission light source that is based on a MCR.

FIG. 6 shows a stimulated emission light source 10d that is based on a MCR. The stimulated emission source 10d includes one or more fluid inputs 12, a CRC 14, and a fluid output 16 for the chemical byproducts of a light emitting chemical reaction. The CRC 14 includes two parallel reflectors 24d, 26, i.e., metallic films. The reflectors 24d, 26 form a Fabry-Perot etalon. One of the reflectors 24d is a partially reflecting optical surface, e.g., 95% reflecting, and the other reflector 26 is a much higher quality optical reflector, e.g., >99%. The partially reflecting optical surface 24d functions as an optical output port for a beam of light produced by the chemical reaction that reactant molecules undergo in the CRC 14. As the intensity of such photons builds in the CRC 14, the high photon intensity resonantly stimulates other reactant molecules to undergo the same reaction thereby optically stimulating emission of photons of the same wavelength. Some emitted photons leave the CRC 14 via the partially reflective reflector 24d thereby producing a beam of stimulated emission light.

In one embodiment, stimulated emission source 10d of FIG. 6 uses a reactant system found in the common firefly, i.e., photonius pyralis. In this embodiment, the input 12 transports an aqueous solution of luciferin, the biological enzyme luciferase, adenosine triphosphate (ATP), and oxygen to the CRC 14. The reactants either mix due to flow obstructions located inside the CRC 14 or are mixed shortly prior to entering the CRC 14. In the CRC 14, the reactants undergo the following enzyme catalyzed reaction chain:

Here, AMP refers to adenosine monophosphate. The reaction chain produces photon with wavelengths in the range of 510 nm to 670 nm. The photons are capable of resonantly stimulating other luciferyl adenylate—luciferase complexes to undergo the second reaction of the reaction chain. For that reason the produced photons optically stimulate emission from the inverted population of luciferyl adenylate—luciferase complexes.

The luciferin-luciferase system has a high efficiency, e.g., about 88%, for converting chemical energy into optical energy. This is higher than the efficiency of typical conventional chemical lasers. For that reason, less heat should be generated by light source 10d than by conventional chemical lasers with the same optical output power. The production of less heat should enable the use of less thermally conductive materials in fabrication of the light source 10d. For example, non-metallic materials may be convenient in embodiments of MCR 10d in which the above reaction causes lasing.

Figure 7:
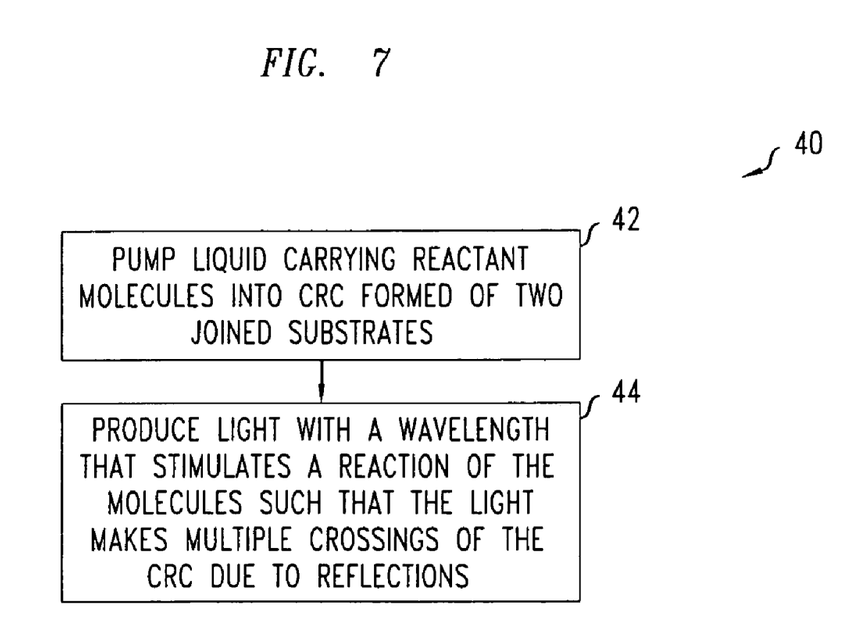
FIG. 7 is a flow chart for a method of operating MCRs such as those of FIGS. 1-6.

FIG. 7 illustrates a method 40 for operating an MCR, e.g., MCRs 10, 10a-10d of FIGS. 1-6. The method 40 includes pumping a liquid carrying dissolved reactant molecules into a CRC formed between joined non-metallic substrates (step 42). The method 40 also includes providing conditions in the CRC to produce a wavelength of light that resonantly stimulates a chemical reaction of the reactant molecules (step 44). The conditions cause the light to make multiple reflections off reflectors located along walls of the CRC while the CRC is filled with the fluid. The reflections thereby cause the light to make multiple crossings of the CRC thereby producing higher photon densities and increasing interaction rates between the light and reactant molecules located in the CRC. The providing step includes either transmitting the light into the CRC via an external window or provoking the chemical reaction, which itself produces the light. The light stimulates the chemical reaction by a resonant interaction with reactant molecules, catalyst molecules, or complexes thereof. The resonant interaction either produces excited molecular states that more rapidly react chemically or optically stimulates same wavelength emissions from molecules participating in the chemical reaction.

Herein, a substrate is a dielectric and/or semiconductor planar structure. Examples of substrates include semiconductor wafers, dielectric wafers, and multi-layered structures. Examples of the multi-layered structures include structures formed by chemically bonding together one or more wafers and structures formed by chemically bonding together one or more processed wafers, wherein the processed wafers have layered structures thereon.

In addition to depending on the fluid flow rate, the size of CRC 14, and the intensity of stimulating light, the reaction rate in a CRC 14 also depends on the form of the optical cavity produced by reflectors 24, 26. An optical cavity that produces a standing wave pattern with a single minimum intensity node in the CRC 14 should provide lower chemical reaction rates than a comparable optical cavity in which the standing wave pattern includes a single maximum and no minimum intensity nodes in the CRC 14. For CRCs 14 whose dimensions are comparable to the stimulating wavelength, optical interference can be used to generate such standing wave patterns.

Conventional microelectronics fabrication techniques are available for making MCRs 10, 10a-10d of FIGS. 1-6. The methods involve fabricating structures on two micro-electronics wafers, i.e., dielectric and/or semiconductor wafers, and then, assembling the two wafers into the MCR. Each of the fabricated structures includes a portion of the CRC. The assembly step involves aligning two portions of the CRC so that the hollow interior of the CRC is formed when the two wafers are joined.

One such fabrication method involves three basic steps. The basic steps include producing a structure on a silica glass wafer, producing a structure on a silicon wafer, and then joining the processed silicon and silica glass wafers to make the MCR. The various steps of the method produce intermediate structures illustrated in FIGS. 8-17 and exemplary final MCRs illustrated in FIGS. 18-19.

The starting silica glass and silicon wafers are available for a variety of sources. The silica glass wafer should include a temperature resistant glass that does not crack when heated to above 400° C., and the glass includes a significant density of incorporated sodium. Exemplary glass wafers are made of borosilicate glass wafers, e.g., having a composition of about 81% $SiO_2$, about 4.0% $Na_2O$, about 0.5% $K_2O$, about 0.5% 13.0% $B_2O_3$, and about 2.0% $Al_2O_3$. Borosilicate glass wafers are sold by Universitywafer, 66 N Street Unit #9, South Boston, Mass. 02127 and Präzisions Glas & Optik GmbH, Hegestück 11 D-58640 Iserlohn, Germany. Suitable conventional silicon wafers are readily available from sources known to those of skill in the art.

Figure 8:
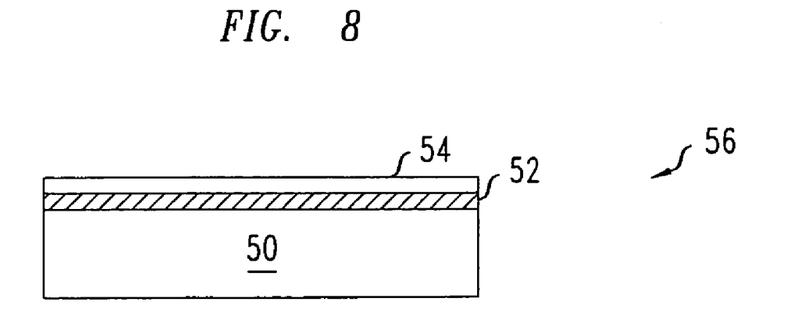
FIGS. 8-17 are cross-sectional views of intermediate structures produced by a microelectronics process for fabricating MCRs.
Figure 9:
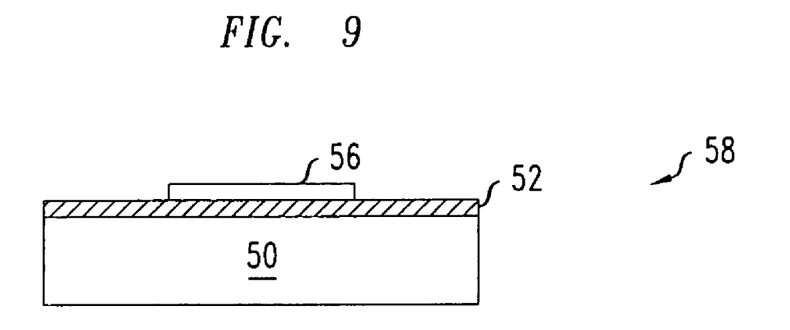
Figure 10:
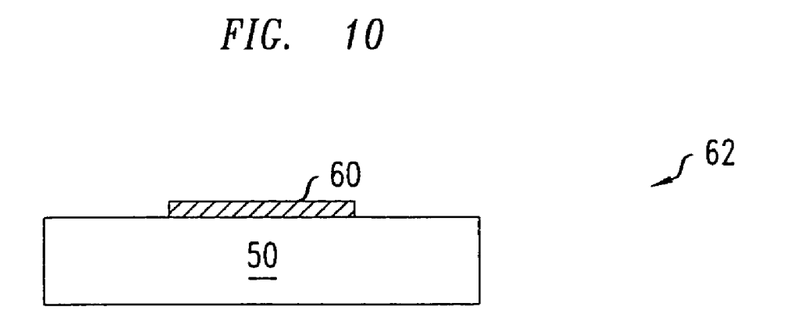
Figure 11:
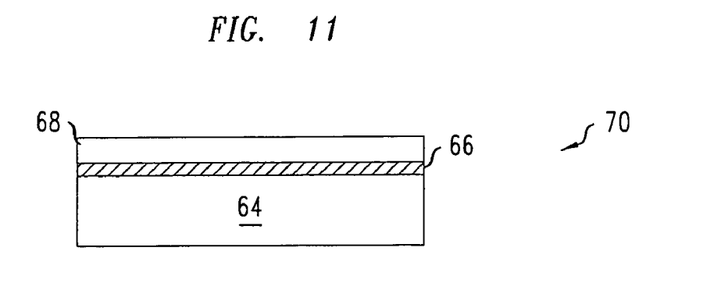
Figure 12:
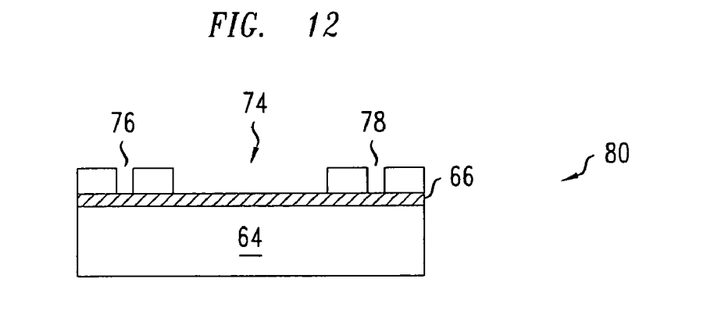
Figure 13:
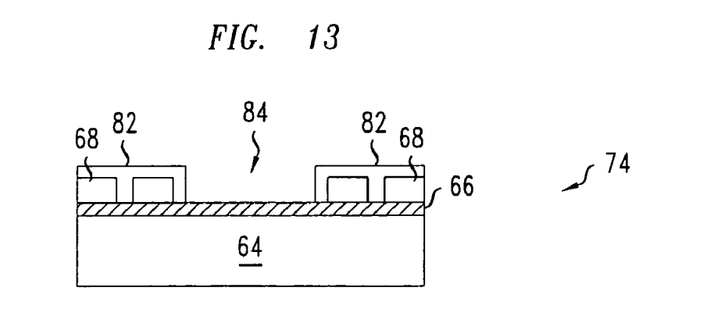
Figure 14:
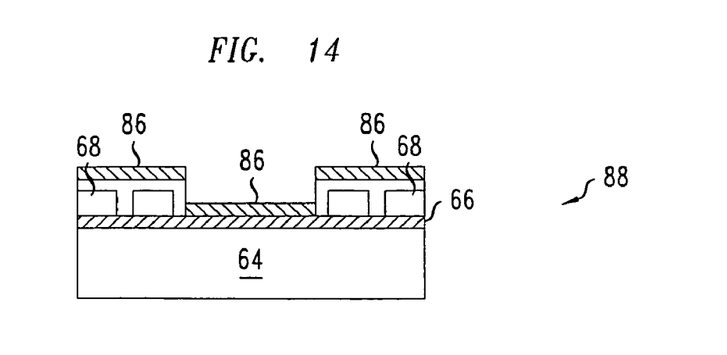
Figure 15:
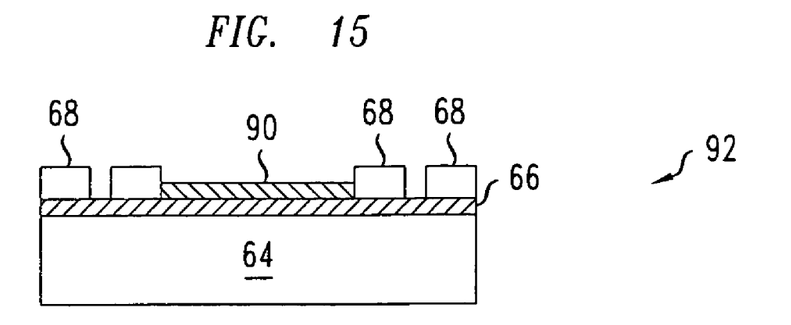
Figure 16:
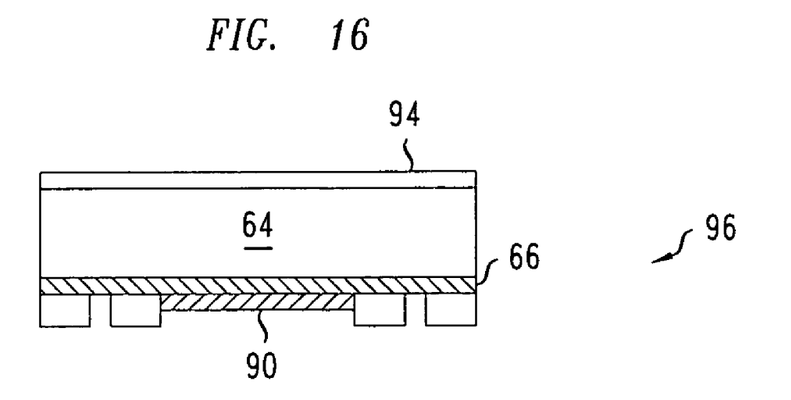

Referring to FIGS. 8-10, several substeps produce the structure on a silica glass wafer 50. The first substep involves depositing a metal film 52 with a thickness of about 40 nanometers (nm) on a planar surface of the silica glass wafer 50 and then, forming a layer 54 of about 300 nm of photoresist on the metal film 52 to produce structure 56. Exemplary metal films 52 include copper, gold, aluminum, or silver. The second substep involves lithographically patterning the layer 54 of photoresist to produce a protective mask 56 over a portion of the metal film 52 as shown in structure 58. The third step involves performing a conventional dry or wet etch to remove unprotected portions of the metallic film 52 and then, performing a conventional reactive ion etch (RIE) or wet etch to strip off the photoresist mask 56. This sequence of substeps produces one metallic reflector 60 of the final CRC on the glass wafer 50 as seen in structure 62.

Referring to FIGS. 11-17, a series of substeps produces a structure on silicon wafer 64. The first substep involves performing conventional depositions to produce a sequence of layers 66, 68. The sequence includes a first layer 66 of about 200 nm of silicon dioxide and a polycrystalline silicon layer 68 as shown in structure 70. The polycrystalline silicon layer 68 has a thickness equal to the desired height, H, of the CRC minus the sum of the thicknesses of the two metallic reflectors. Since microelectronics deposition techniques are able to produce polycrystalline silicon layers with a thickness of about 30 microns or less, the final CRC will have a height, H, of not more than about 30 microns. The second substep involves conventionally patterning the polycrystalline silicon layer 68 to produce a portion of CRC 74 and portions of the fluid inputs and outputs 76, 78 as shown in structure 80. The patterning substep also may produce flow obstructions (not shown) and a fluid mixing chamber (not shown) if such features are desired in the MCR. The third substep involves lithographically making a protective photoresist mask 82. The photoresist mask 82 includes a rectangular window 84 over a region of polycrystalline silicon layer 66 where the second reflector and half of the CRC will be made. The window 84 has lateral widths W and W' with W being between 10 microns and 500 microns and being preferably about 200, and W' being between 50 microns and 300 microns and being preferably about 100 microns. The fourth substep involves performing an evaporation deposition of a metal film 86 for the second reflector as shown in structure 88. Exemplary metal films include copper, gold, aluminum, or silver. The fifth substep involves performing a wet etch to strip away the photoresist mask 82 thereby exposing the second reflector 90 of the CRC as shown in structure 92. The wet etch may use acetone or the EKC265 resist stripper made by EKC Technology, Danville, Calif. 94526 USA. The sixth substep involves flipping the silicon wafer 64 over and forming a photoresist layer 94 on the backside of the silicon wafer 64 as shown in structure 96. The seventh substep involves performing another lithographic process to produce a photoresist mask from the photoresist layer 94. The photoresist mask includes windows for the one or more fluid inputs 98 and a fluid output 100. The final step involves performing a conventional deep etch through the silicon wafer 64 to produce the fluid output 100 and the one or more fluid inputs 98 and then, performing the above-described wet etch to strip away the photoresist mask and produce structure 102.

Figure 17:
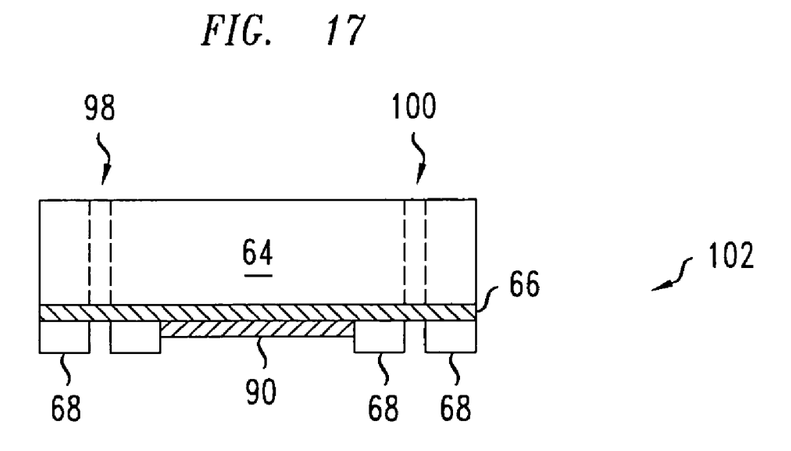

Referring to FIGS. 17 and 10, joining the processed silicon wafer, i.e., structure 102, and the processed silica glass wafer, i.e., structure 62, produces the final MCR. Depending on the dimensions of the first reflector 60, the final MCR either has the structure 104 of FIG. 18 or has the structure 106 of FIG. 19. In the MCR 104, the first reflector 60 covers one entire wall of the CRC 14 so that external light cannot be introduced therein through the transparent glass wafer 50. In the second MCR 106, the first reflector 60 covers only a portion of one wall of the CRC 14 so that a transparent silica glass window 22 remains for introducing external light into the CRC 14, e.g., as in MCR 10a of FIG. 2.

Figure 18:
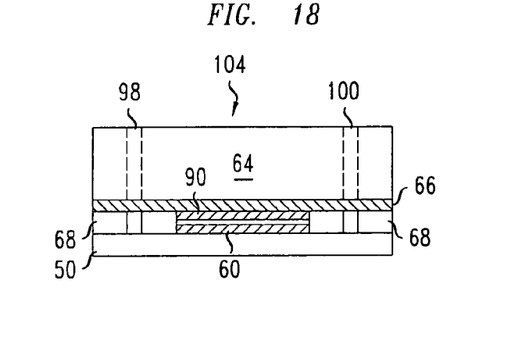
FIGS. 18-19 are cross-sectional views of MCRs that were fabricated from the intermediate structures of FIGS. 10 and 17.
Figure 19:
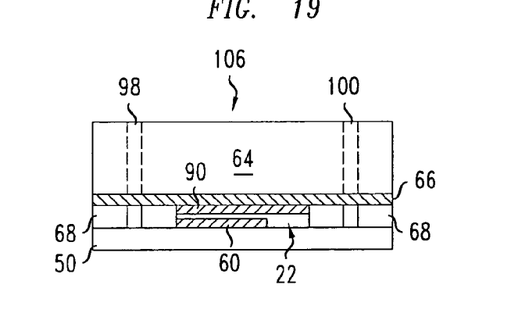

The joining step involves optically aligning the processed silicon and silica glass wafers 102, 62 such that the two reflectors 60, 90 are suitably aligned and, then bonding the processed wafers 62, 102 together. In MCR 104, a suitable alignment enables light to make multiple reflections off reflectors 60 and 90. In MCR 106, a suitable alignment ensures that light may enter through transparent silica glass window 22 and then make multiple reflections off reflectors 60 and 90. The alignment substep uses optical alignment marks on the silicon and silica glass wafers 64, 50. The alignment marks on the silicon wafer 64 are viewed through the silica glass wafer 50 during the alignment step. The bonding substep involves performing an anodic bonding of the two wafers 62, and 102. In anodic bonding, the two processed wafers 62, 102 are clamped and placed between metal electrodes. Then a high DC voltage, e.g., more than about 1000 voltages, is applied across the electrodes. The voltage heats the contacting surfaces of the wafers 62, 102 to about 400° C. The original glass wafer 50 is selected to have sodium ions present therein. The high temperature displaces the sodium ions from the surface of the glass wafer 50. The displacement makes the glass surface very reactive and forms a chemical bond between the two wafers 50, 64.

In other embodiments, a variation of the above fabrication method involves processing two silicon wafers to produce structures thereon and then joining the processed silicon wafers to make one or more MCRs. For intermediate structures formed on two silicon wafers, the assembly step involves a fusion bonding process. In the fusion bonding process, the two silica wafers are brought in intimate contact by applying a high contact force. Once in intimate contact, Van der Waals forces bonds the silicon wafers together firmly enough for handling. Then, the bonded wafers are annealed in a high temperature oven to produce a chemical bond there between.

In the above-described embodiment in which the MCR was assembled from a processed glass wafer 62 and a processed silicon wafer 102, the CRC has a height, H, of about 30 microns or less. The height, H, of the CRC is limited by the thickness of silicon dioxide layer 68. Such layers are typically difficult to deposit to thicknesses of greater than about 30 microns. This implies that the above-described method will produce MCRs with heights of about 30 microns or less.

Other microelectronics processing methods are available for forming CRCs with larger heights. One such method involves performing a deep etch in a silicon wafer to form a deep hollow chamber and then, bonding the etched silicon wafer to a second silicon or silica glass wafer to form the CRC. Techniques for forming chambers by joining a deeply etched silicon wafer to a second waver are known in the art. For example, methods for forming such structures are described in U.S. Pat. No. 5,589,136, issued Dec. 31, 1996, which is incorporated by reference herein in its entirety. In light of the above description, one of skill in the art would be able to fabricate other MCRs in which deep etching methods were used to form one or both halves of the CRC. In such embodiments, the height, H, of CRC may be as large as 750 microns.

In light of the above description, one of skill in the art should be able to fabricate CRCs with higher heights by using deep etching or by joining together three or more dielectric and/or silicon wafers.

Figure 20:
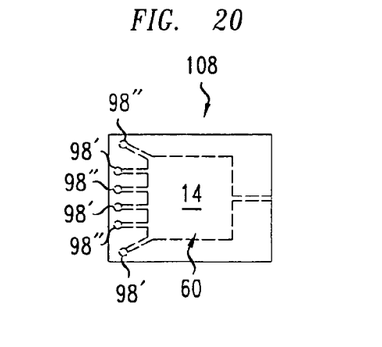
FIG. 20 is a top view of a section through a MCR in which two types of fluid inputs are inter-dispersed along one edge of the CRC.
Figure 21:
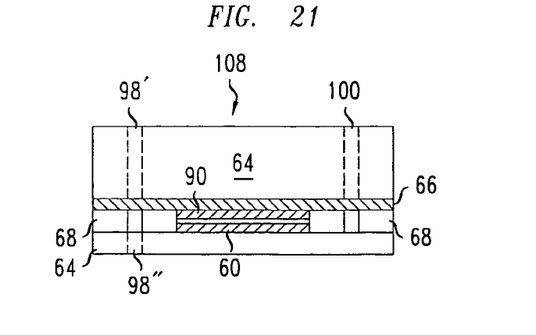
FIG. 21 is a cross-sectional view of the MCR of FIG. 20.

FIGS. 20 and 21 shows another MCR 108 fabricated with microelectronics processes similar to those used to make MCRs 104 and 106 of FIGS. 17 and 18. In the MCR 108, inputs 98' and inputs 98" have alternating positions along the edge of CRC 14. Due to the alternating positions, fluids from the two types of inputs, i.e., 98' and 98", mix upon entering into the CRC 14. The inputs 98' and 98" pass through front and back silicon wafers 64 and 64', respectively.

Other embodiments of MCRs 104, 106 use wafers that made from different dielectrics and/or semiconductors than silica glass and silicon.

From the disclosure, drawings, and claims, other embodiments of the invention will be apparent to those skilled in the art.

What is claimed is:

1. A chemical reactor, comprising:
    two substrates being joined and being in contact along a surface external to a chemical reaction chamber, each substrate comprising dielectric or semiconductor and being a planar structure, the chemical reaction chamber being formed between the substrates, the chemical reaction chamber having a hollow interior; and
    a plurality of light reflectors located along facing walls of the hollow interior, the chemical reaction chamber having one or more inputs to transport fluid into the hollow interior and an output to transport fluid out of the hollow interior; and
    wherein the light reflectors are configured to cause light rays to make multiple crossings of the hollow interior by making multiple reflections off the light reflectors.

2. The chemical reactor of claim 1, wherein one or more of the substrates comprises a plurality of wafers that are chemically bonded together along surfaces thereof.

3. The chemical reactor of claim 1, wherein the chemical reaction chamber comprises a plurality of physical flow obstructions positioned to cause a first fluid received from a first of the one or more inputs and a second fluid received from a second of the one or more inputs to mix.

4. The chemical reactor of claim 1, further comprising a window transparent to at least one wavelength of light and located in one of the substrates, the window being positioned to transmit external light rays into the reaction chamber such that the transmitted light rays make multiple reflections off the reflectors.

5. The chemical reactor of claim 4, further comprising a chemical catalyst located on a portion of the walls of the reaction chamber.

6. The chemical reactor of claim 4, wherein the plurality of light reflectors includes one of a metallic reflector and a wavelength-selective multilayer interference reflector.

7. The chemical reactor of claim 6, wherein the light reflectors include a protective dielectric coating thereon, the coating being located between the light reflectors and the hollow interior.

8. The chemical reactor of claim 1, wherein the plurality of light reflectors includes a pair of metallic reflectors with substantially parallel surfaces.

9. The chemical reactor of claim 8, wherein the pair of reflectors forms a Fabry-Perot etalon.

10. The chemical reactor of claim 9, wherein one of the reflectors of the pair functions as an optical output port for light produced in the cavity.

11. The chemical reactor of claim 8, wherein the reaction chamber is a planar structure whose lateral width is less than about 0.5 millimeters.

12. The chemical reaction chamber of claim 1, wherein one of the substrates is an optically transparent dielectric.

13. A process for operating a chemical reactor, comprising:
    pumping a liquid having dissolved reactant molecules into a chemical reaction chamber formed between two joined substrates, the substrates including dielectric and/or semiconductor, each substrate being a planar structure, the substrates being in contact along a surface exterior to the chemical reaction chamber; and providing conditions in the chemical reaction chamber that produce a wavelength of light that stimulates a chemical reaction of the reactant molecules, the light undergoing multiple reflections off a plurality of light reflectors located along facing walls of the chemical reaction chamber, the reflections causing the light to make multiple crossings of the chemical reaction chamber.

14. The process of claim 13, wherein the reaction produces light and a portion of the light produced by the reaction undergoes multiple reflections off the light reflectors.

15. The process of claim 13, wherein the pumping causes the fluid to enter the chemical reaction chamber, three linear dimensions of the chemical reaction chamber being less than about 1 mm.

16. The process of claim 13, wherein the providing includes transmitting external light into the chemical reaction chamber via a window, a portion of the transmitted light making multiple reflections off the light reflectors and having a wavelength that resonantly stimulates the reaction.

17. The process of claim 13, wherein the plurality of light reflectors comprises a pair of reflectors; and wherein the providing causes a beam of stimulated emission light to traverse one reflector of the pair.

18. The process of claim 17, wherein the pair of reflectors forms a Fabry-Perot etalon.

* * * * *